United States Patent [19]

Lemon et al.

[11] Patent Number: 5,090,902
[45] Date of Patent: Feb. 25, 1992

[54] MULTI-MEASURMENT PERIODONTAL PROBE

[75] Inventors: J. Robert Lemon, Charlotte; William T. Evans; Robert E. Christian, both of Batesville, all of Ark.; Herbert J. Bader, Sharon, Mass.

[73] Assignee: Professional Dental Technologies, Corp., Batesville, Ark.

[21] Appl. No.: 669,069

[22] Filed: Mar. 12, 1991

[51] Int. Cl.[5] ............................................. A61C 19/04
[52] U.S. Cl. .......................................... 433/72; 33/514
[58] Field of Search .................. 433/72, 75, 141, 215; 128/776; 33/513, 514

[56] References Cited

U.S. PATENT DOCUMENTS

| | | | |
|---|---|---|---|
| 3,058,225 | 10/1962 | Ward | 128/776 |
| 4,203,223 | 5/1980 | Lautenschlager et al. | 433/75 |
| 4,445,857 | 5/1984 | Borst | 433/75 |
| 4,552,531 | 11/1985 | Martin | 433/141 |
| 4,823,809 | 4/1989 | Gott, Jr. et al. | 33/514 |
| 5,000,683 | 3/1991 | Brock | 433/72 |

FOREIGN PATENT DOCUMENTS 9011046 10/1990 PCT Int'l Appl. .................. 128/776

Primary Examiner—Cary E. O'Connor
Attorney, Agent, or Firm—William J. Sapone

[57] ABSTRACT

A multi-measurement periodontal probe (5) has a probing portion (7) which utilizes a needle-like tip (8) to determine the depth of a periodontal pocket. The probe additionally has a measurement member (9) extending opposite to the needle-like tip. The measurement member has gradations or other markings for determining the distance between an occlusal tooth surface and the bottom of the periodontal pocket, at the same time that the depth of the periodontal pocket is determined from the gumline. The use of such a probe allows determining whether periodontal disease is progressing while eliminating the bias encountered with changes in the gumline which may occur as a consequence of periodontal disease. Utilizing such a probe assures that accurate readings are taken and improves the accuracy of the diagnosis of periodontal disease.

20 Claims, 2 Drawing Sheets

MULTI-MEASURMENT PERIODONTAL PROBE

CROSS-REFERENCE TO RELATED APPLICATION

This application is related to co-assigned, co-pending application Ser. No. 603,638 filed Oct. 25, 1990 (pending) and titled "Constant Pressure Periodontal Probe".

1. Technical Field

This invention is related to periodontal probes and more particularly to a periodontal probe having a measurement extension for taking multiple measurements during probing.

2. Background

Periodontal probes are used to test the depth of a pocket which exists between a tooth and gum. The pocket is formed as a result of progressive gingival inflammation and loss of attachment. Once formed, the periodontal pocket provides a sheltered environment for pathogenic microbial colonies, which may cause further connective tissue damage. The depth measurement is one diagnostic method to determine whether periodontal disease is or has been present and to what extent; the deeper the pocket, the more apical the attachment between the tooth and gum and more likely it is that treatment is required.

Typical periodontal probes, shown for example in U.S. Pat. Nos. 4,768,952, 4,886,454, and 4,764,114, use a needle-like tip for determining pocket depth. The tip is inserted between the tooth and gum until the bottom of the pocket is reached, with the tester relying on the resistance to insertion to feel the bottom of the pocket. The tip usually has markings to indicate the depth of the pocket relative to the gumline. Pocket depth over about 3 millimeters indicate that treatment should be undertaken. Multiple readings may be taken around each tooth and a history developed to note changes in pocket depth to determine if progressive pocket enlargement is occurring or has occurred since the last examination.

A problem with periodontal probing is that it is difficult to judge the changes over time which occur in pocket depth because of possible changes in the gumline. For example, the gumline may recede at an equivalent rate to match that of the increased depth of the periodontal pocket. Consequently, the probing may indicate a constant pocket depth when in fact additional attachment loss has occurred.

DISCLOSURE OF INVENTION

It is an object of the present invention to provide a multi-measurement periodontal probe which in a single insertion measures pocket depth relative to the gumline, and the pocket depth relative to the occlusal (top) surface of the toot being examined.

It is a further object to provide a periodontal probe which indicates changes in the gumline relative to the occlusal tooth surface which is a fixed reference point with time.

It is a further object to provide a measurement extension on a constant pressure periodontal probe to improve measurement accuracy.

These and other objects of the present invention are achieved by providing a periodontal probe having a handle, a probing portion extending from the handle, the probing portion having a needle-like tip for insertion between the tooth and gum. A measurement member extends upwardly opposite to the needle-like tip. The member has markings or other gradations for reading the distance from the bottom of the pocket to the gumline and the bottom of the pocket to the occlusal surface of the tooth. Thus, during probing, a dentist can determine the pocket depth, relative to the gumline, and the pocket depth relative to the top of the tooth. By mathematical calculations, he can also determine the measurement of the distance between the gum line and the top of the tooth. By maintaining a history of these measurements, a more accurate diagnosis of periodontal disease can be determined.

DETAILED DESCRIPTION OF THE INVENTION

Figure 1:
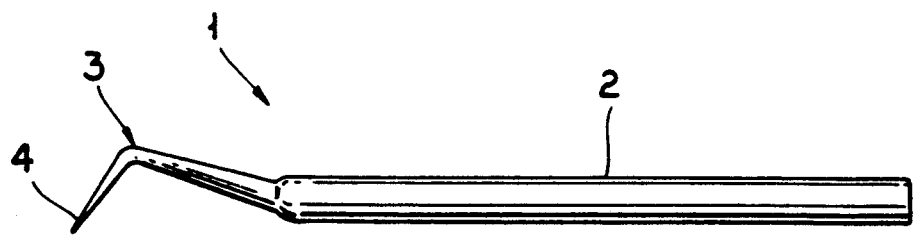
FIG. 1 is a view of a prior art periodontal probe.

Referring to FIG. 1, a typical prior art periodontal probe 1 has a handle 2, a probing portion 3 and a needle-like tip 4. The handle may be round or shaped to provide effective hand manipulation and the probe may be angled, relative to the handle to ease probing. Usually, the probe tip will have gradations or other markings to indicate pocket depth. The probe may be made of plastic or metal.

Figure 2:
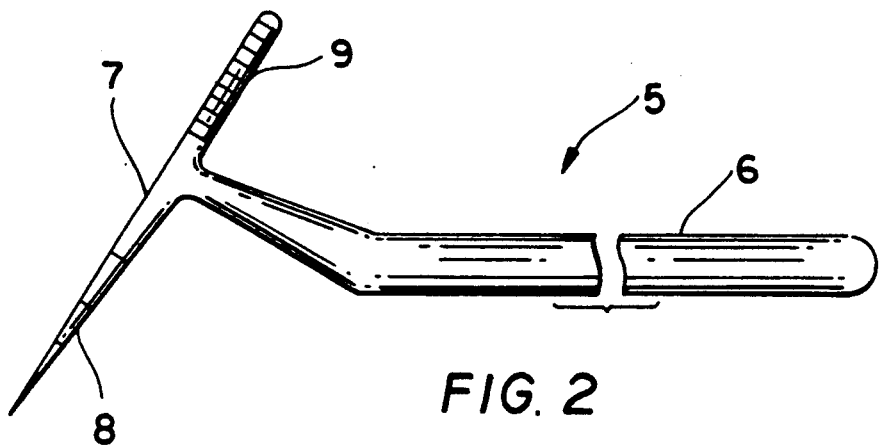
FIG. 2 is the periodontal probe of the present invention having a measurement member.

Referring to FIG. 2, the probe of the present invention is shown. The probe 5 has a handle 6, a probing portion 7 and a needle-like tip 8, similar to those described previously. However, the probe additionally has a member 9 extending opposite to the tip 8, in an amount sufficient to determine the distance between the occlusal tooth surface and the bottom of the pocket. The member 9 has gradations to indicate the distance, for example, in millimeters, however, other markings could be used. By measuring from the occlusal surface of the tooth, long term accuracy is assured as erosion of the tooth surface will normally progress quite slowly. This contrasts with the gumline which may vary with time due to the presence or absence of disease or inflammation.

While the member 9 is coaxial with the probe tip 8, this need not be the case, and an offset member which allows reading, during a single insertion, the pocket depth to the top of the tooth is believed to fall within the scope of the present invention. The member may be cylindrical, flat or of any other shape, convenient for reading the pocket depth.

Figure 3:
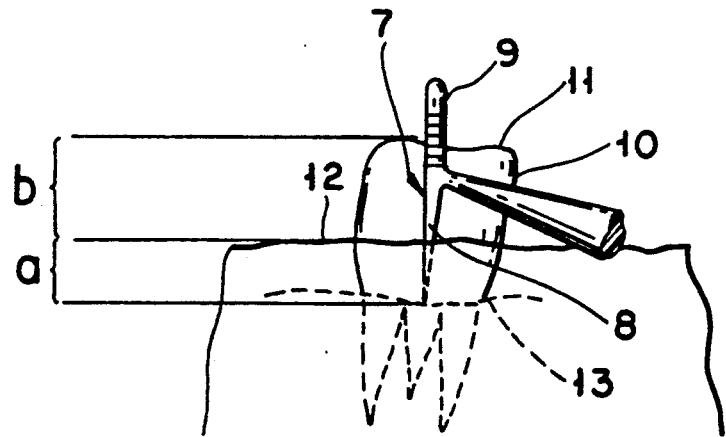
FIG. 3 is an illustrative view showing the probing of a periodontal pocket by the probe of FIG. 2.

Referring to FIG. 3, the probe 7 is shown probing a periodontal pocket. A tooth 10 has a occlusal surface 11, a gumline 12 and an attachment line 13. The periodontal pocket extends from the gumline to the attachment line, as indicated by measurement "a". The probe tip 8 is inserted until the tip contacts the attachment line, as shown. The depth is then read from the markings on the tip. In addition, the distance from the attachment line 13 to the occlusal surface 11 is determined by reading from the measurement extension 9, as indicated by measurement "b". Thus, pocket depth is determined from two points, which over time, with periodic testing, can confirm the progression of periodontal disease, if any, without the inaccuracies encountered by using the gumline as the base for measurement.

The inventive probe is composed of metal or plastic. Among the materials of construction contemplated are acrylic polymers, polyethylene, polypropylene, nylon, polystyrene, polyurethane, polyetherimid (ULTEM TM), steel, stainless steel, or combinations thereof. ULTEM is preferred as it has good strength properties while being sufficiently high temperature resistant to allow sterilization.

Figure 4:
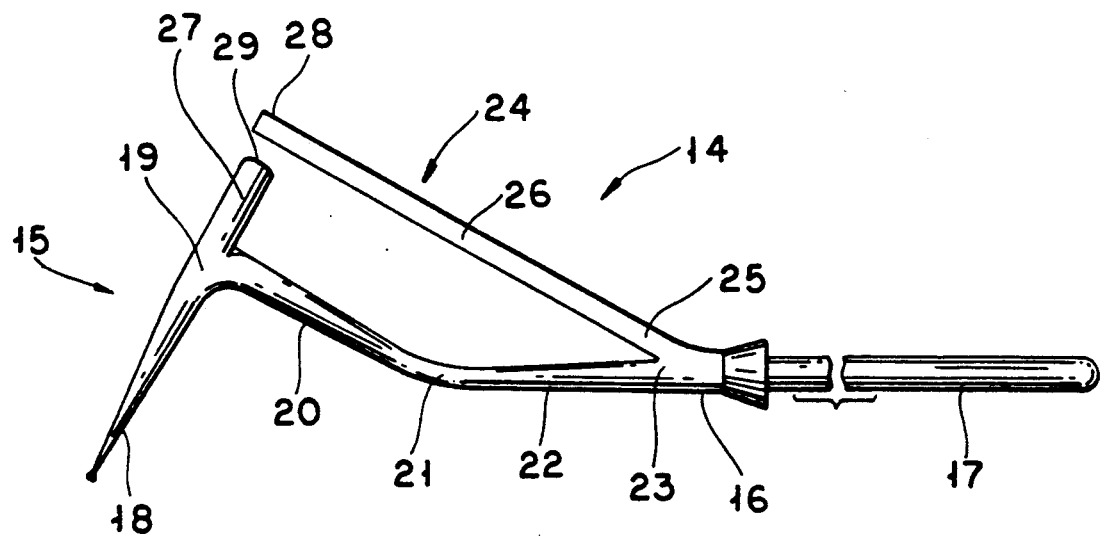
FIG. 4 is an alternative embodiment of the present invention incorporating the measurement member on a constant pressure periodontal probe.

In another embodiment of the present invention, shown in FIG. 4, the periodontal probe is a constant pressure periodontal probe as described in co-pending application Ser. No. 603,638, titled CONSTANT PRESSURE PERIODONTAL PROBE, filed Oct. 25, 1990 and co-assigned herewith. Disclosure of the application is incorporated herein by reference.

Referring still to FIG. 4, a probe 14 has a probing portion 15 joined at a junction 16 to a handle 17. The probing portion includes a needle-like tip 18 which extends from a corner 19. The corner 19 is attached to a first rigid section 20 to a flexing joint 21 through a second rigid section 22 to a junction 23. The flexing joint 21 provides a focal point for probe displacement when resistance to insertion is met. The flexing joint is tapered and shaped to provide the weakest point between the sections 20 and 22 such that resistance to probing causes the probe to travel in an arc about the flexing joint.

A backing portion 24 is joined at an end 25 through the junction 23 to the handle 17. The backing portion has a rigid arm 26 extending substantially parallel to the first section 20 of the probing portion, extending adjacent to but spaced away from the probing portion Both portions are in alignment. The arm 26 has sufficient rigidity to stop movement of the probing portion when a force of greater than the desired probing insertion force is applied. This rigidity can be adjusted by increasing the thickness of the arm relative to the thickness of the probing portion.

The probing portion 15 also has a measurement member 27, which extends from the corner 19 upwardly and opposite to the probing tip. Thus, the rigid arm 26 is disposed slightly behind the measuring member 27. The backing portion 24 has a tip end 28 which is spaced away from an end 29 of the member, to provide a gap therebetween. The gap is sized to accommodate movement of the probing portion as the resistance to insertion causes the probing portion to move about the joint 21, with contact between the end 29 and the tip 28 indicating that the desired testing pressure has been reached. The backing tip provides a stop for receiving the end 29.

Figure 5:
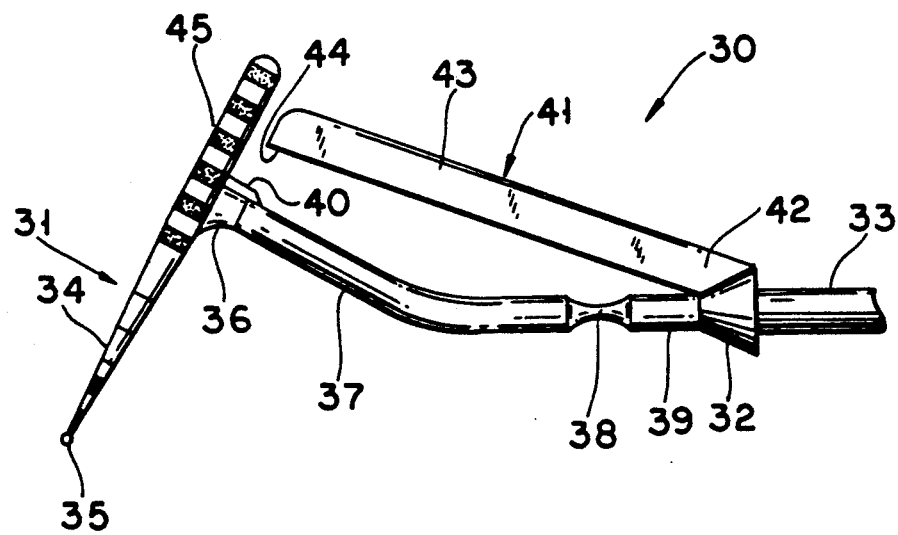
FIG. 5 is another alternative embodiment of the present invention incorporating the measurement member on a constant pressure periodontal probe.

Referring to FIG. 5, another alternative embodiment of the present invention utilizing a constant pressure periodontal probe is shown. A probe 30 has a probing portion 31 joined at a junction 32 to a handle 33. The probing portion has a needle like tip 34 with a ball end 35 which extends from a corner 36. The needle like tip has contrasting regions to denominated measurement units such as millimeters. The corner is connected to a first rigid section 37 to a flexing joint 38 through a second rigid section 39 to the junction 32. An upwardly extending projection 40 is positioned just behind the corner on the first rigid section. The flexing joint is similar in operation to the one previously described.

A backing portion 41 is joined at an end 42 through the junction 32 to the handle 33. The backing portion has a rigid arm 43 extending somewhat parallel to a forward portion of the first section 37, extending adjacent to but spaced away from the probing portion. The arm is at least in alignment with the first section 37. The arm has sufficient rigidity to stop movement of the probing portion when contacted. The degree of rigidity can be adjusted by increasing or decreasing the thickness of the arm. A tip 44 of the backing portion is spaced away from the projection 40 to provide a gap therebetween. The gap is sized to accommodate movement of the probing portion as the resistance to insertion causes the probing portion to move about the joint 38, with contact between the projection and the tip indicating that the desired testing pressure has been reached.

The probing portion 31 has a measurement member 45 which extends from the corner 36 upwardly and opposite to the probing tip. The member has contrasting areas to denominated measurement units, such as millimeters. The projection 40 and tip 44 are disposed slightly behind the measurement member to prevent contact between the measurement member and the backing arm. This allows the gap to be adjusted independently of the length of the measurement member, and allows the probing portion to travel in a proscribed arc without interference.

The constant pressure periodontal probe works by standardizing insertion pressure when probing the attachment level and thus yields reproducible readings of pocket depth. The combination of the constant pressure periodontal probe with the measurement member increases the accuracy of the measurement of pocket depth relative to both the gumline and the occlusal tooth surface and increases the accuracy of diagnosis of periodontal disease. Since the records taken will be more reproducible, it is more likely to yield accurate indications of changes in attachment level, while also eliminating the variances from one clinician to another based on probing force as well as variations by the same clinician from examination to examination.

This invention makes it possible for all examiners to provide meaningful data to a centralized source which avoids the bias inherent with present testing methods due to variations in applied force and changes in the gum line.

The probe is preferably produced as a unitary structure to minimize cost and allow mass production. However, it is contemplated that the probe tip may be separably produced and be removable from the corner to allow replacement. Since the measurement member is non-invasive, it is not likely that this would need to be removed. However, should a multi-purpose tool be desired, it is possible that the measurement extension could also be separably produced and removable from the probe handle.

While preferred embodiments of the present invention have been shown and described, it will be understood by those skilled in the art that various changes or modifications could be made without varying from the scope of the present invention.

We claim:

1. A periodontal probe comprising a handle, a probing portion extending from the handle, and a needle-like tip extending from the probing portion, a measurement member placed opposite to the needle-like tip, the measurement member being of sufficient length to extend above an occlusal tooth surface during probing to indicate the distance between the bottom of a periodontal pocket and the occlusal tooth surface, a rigid backing portion extending from the handle adjacent to but spaced away from the measurement member by a gap, a flexing joint provided in the probing portion, the flexing joint allowing the probing portion to be displaced as resistance to insertion increases, the backing portion providing a stop to limit displacement of the probing portion, contact between the backing portion and the measurement member indicating that a desired insertion pressure has been reached.

2. The probe of claim 1 wherein the probing portion has a corner, the needle-like tip extending from the corner in a downwardly direction, the measurement member extending opposite to the tip in an upward direction for a distance sufficient to measure the distance between the bottom of the periodontal pocket and the occlusal tooth surface, first and second rigid sections disposed on opposite sides of the flexing joint in an angular relationship, the first section connected to the corner and the second section connected to the handle.

3. The probe of claim 1 wherein the probe is composed of a material from the group consisting essentially of acrylic polymers, polyethylene, polypropylene, nylon, polystyrene, polyurethane, polyetherimid, steel and stainless steel.

4. The probe of claim 1 wherein the measurement member has gradations to indicate measurement units.

5. The probe of claim 1 wherein the measurement member has contrasting regions to indicate measurement units.

6. The probe of claim 1 wherein the measurement member is round.

7. The probe of claim 1 wherein the measurement member is flat.

8. A periodontal probe comprising a handle, a probing portion extending from the handle, and a needle-like tip extending from the probing portion, a measurement member placed opposite to the needle-like tip, the measurement member being of sufficient length to extend above an occlusal tooth surface during probing to indicate the distance between the bottom of a periodontal pocket and the occlusal tooth surface, a rigid backing portion extending from the handle adjacent to but spaced away from the probing portion by a gap, a flexing joint provided in the probing portion, the flexing joint allowing the probing portion to be displaced as resistance to insertion increases, the backing portion providing a stop to limit displacement of the probing portion, contact between the backing portion and the probing portion indicating that a desired insertion pressure has been reached.

9. The probe of claim 8 wherein the probe is composed of a material of the group consisting of acrylic polymers, polyethylene, polypropylene, nylon, polystyrene, polyurethane, polyetherimid, steel, and stainless steel.

10. The probe of claim 8 wherein the measurement member has gradations to indicate measurement units.

11. The probe of claim 8 wherein the measurement member has contrasting regions to indicate measurement units.

12. The probe of claim 8 wherein the measurement member is round.

13. The probe of claim 8 wherein the measurement member is flat.

14. A method for testing for periodontal disease comprising:
providing a periodontal probe comprising a handle, a probing portion extending from the handle, and a needle-like tip extending from the probing portion, a measurement member placed opposite to the needle-like tip, the measurement member being of sufficient length to extend above an occlusal tooth surface during probing to indicate the distance between the bottom of a periodontal pocket and the occlusal tooth surface;
inserting the probing portion between a gum and a tooth until the needle-like tip contacts the bottom of a periodontal pocket,
reading the depth of insertion into the gum when contact is made with the bottom of the pocket and,
reading the distance between the bottom of the pocket and an occlusal surface of the tooth.

15. A periodontal probe comprising a handle, a probing portion extending from the handle, and a needle-like tip extending downwardly from the probing portion, a measurement member placed opposite to the needle-like tip, extending upwardly from the probing portion, the measurement member being of sufficient length to extend above an occlusal tooth surface during probing to indicate the distance between the bottom of a periodontal pocket and the occlusal tooth surface.

16. The probe of claim 15 wherein the probe is composed of material from the group consisting of acrylic polymers, polyethylene, polypropylene, nylon, polystyrene, polyurethane, polyetherimid, steel, and stainless steel.

17. The probe of claim 15 wherein the measurement member is round.

18. The probe of claim 15 wherein the measurement member is flat.

19. The probe of claim 15 wherein the measurement member has gradations to indicate measurement units.

20. The probe of claim 15 wherein the measurement member has contrasting regions to indicate measurement units.

* * * * *